(12) United States Patent
Nakada

(10) Patent No.: US 7,260,481 B1
(45) Date of Patent: Aug. 21, 2007

(54) VECTOR DETECTING DEVICE AND LIVING-BODY COMPLEX IMPEDANCE MEASURING APPARATUS HAVING THE VECTOR DETECTING DEVICE

(75) Inventor: Masato Nakada, Schaumburg, IL (US)

(73) Assignee: Tanita Corporation, Tokyo (JP)

(*) Notice: Subject to any disclaimer, the term of this patent is extended or adjusted under 35 U.S.C. 154(b) by 25 days.

(21) Appl. No.: 11/377,453

(22) Filed: Mar. 17, 2006

(51) Int. Cl.
*G01N 33/48* (2006.01)

(52) U.S. Cl. .......................... 702/19; 702/65; 600/547

(58) Field of Classification Search .................. 702/19, 702/65; 324/692
See application file for complete search history.

(56) References Cited

U.S. PATENT DOCUMENTS 7,161,362 B2 * 1/2007 Shambroom et al. ....... 324/692

FOREIGN PATENT DOCUMENTS

| JP | 4-80667 A | 3/1992 |
|---|---|---|
| JP | 4-109174 A | 4/1992 |

* cited by examiner

*Primary Examiner*—Hal Wachsman
*Assistant Examiner*—Stephen J. Cherry
(74) *Attorney, Agent, or Firm*—McDermott Will & Emery LLP

(57) ABSTRACT

A phase-sensitivity detector detects a phase sensitivity of an AC signal with a known frequency, output by an input amplifier, and an integrator double-integrates an output of (X-Y) of which the phase sensitivity is detected, thereby obtaining vector detecting information $\alpha(tend-tst)/tm=A \cos\theta$ and $\alpha(tend-tst)/tm=A \sin\theta$ of the AC signal with the known frequency.

4 Claims, 6 Drawing Sheets

VECTOR DETECTING DEVICE AND LIVING-BODY COMPLEX IMPEDANCE MEASURING APPARATUS HAVING THE VECTOR DETECTING DEVICE

BACKGROUND OF THE INVENTION

1. Field of the Invention

The present invention relates to a vector detecting device that detects a vector of an AC signal with known frequency. More particularly, the present invention relates to a living-body complex impedance measuring apparatus that measures living-body impedance by detecting a vector of a signal from a living body in which an AC signal having a known frequency flows.

2. Description of the Related Art

Conventionally, in a vector detecting device that detects a vector of an output as a target, and an impedance measuring apparatus that measures impedance of which a vector is detected, a phase detector detects a vector of an, output from a measuring target, an integrator smoothes and integrates the output of which the vector is detected, and an A/D converter converts an analog output which is smoothed and integrated into a digital signal (see, e.g., Japanese Unexamined Patent Application Publication No. 4-80667 (Patent Document 1) and Japanese Unexamined Patent Application Publication No. 4-109174 (Patent Document 2)).

However, in the above-described conventional apparatus, the integrator integrates the output only to amplify the detected vector from the phase detector. Therefore, in the conventional apparatus, an offset voltage of the integrator is generated and, disadvantageously, an expensive A/D converter is needed independent of the integrator.

SUMMARY OF THE INVENTION

To solve the above-mentioned problem of conventional devices, it is one object of the present invention to provide a low-cost vector detecting device in which generation of an offset voltage of the integrator is prevented and the vector of the target output is detected. It is another object of the present invention to provide a low-cost living-body complex impedance measuring apparatus in which generation of the offset voltage of the integrator is prevented, and living-body impedance is measured by detecting the vector of the target output.

According to one aspect of the present invention, a vector detecting device comprises a first reference-potential generating unit that generates a first reference-potential; an input amplifier that receives an AC signal with a known frequency, amplifies or buffers, and outputs the AC signal; a phase-sensitivity detector that detects a phase sensitivity of the amplified or buffered AC signal output by the input amplifier using the first reference-potential as a reference, a second reference-potential generating unit that generates a second reference-potential lower than the first reference-potential; a charge/discharge change-over switch that switches the connection between the first reference-potential and the second reference-potential and the AC signal of which the phase sensitivity has been detected by the phase-sensitivity detector; an integrator that integrates the AC signal of which the phase sensitivity has been detected, from the charge/discharge change-over switch, and outputs an integrated potential; a third reference-potential generating unit that generates a third reference-potential higher than the first reference-potential; a comparator that outputs signals at levels varying depending on whether the potential output and integrated by the integrator is higher than the third reference-potential or lower than the third reference-potential; an integrating-time timer unit that counts an outputting time of the potential integrated by the integrator; a sync-signal control unit that outputs to the phase-sensitivity detector two types of phase signals synchronous with the AC signal with a constant phase thereof; a charge/discharge control unit that outputs to the charge/discharge change-over switch a control signal for switching the connection between the first reference-potential and the second reference-potential and the AC signal of which the phase sensitivity has been detected, to charge the integrator until the time counted by the integrating-time timer unit reaches a predetermined time from a charging start time and, thereafter, a control signal for switching the connection between the first reference-potential and the second reference-potential and the AC signal of which the phase sensitivity has been detected, to discharge the integrator until the levels of the signals output by the comparator change; and a vector-detecting-information calculating unit that calculates the vector detecting information of the AC signal received by the input amplifier on the basis of a time which reaches the predetermined time from the charging start time counted by the integrating-time unit when the charge/discharge control unit outputs to the charge/discharge change-over switch the control signal for switching the connection to charge the integrator, the time counted by the integrating-time timer unit when the charge/discharge control unit outputs to the charge/discharge change-over switch, the control signal for switching the connection to discharge the integrator when the levels of the signals output by the comparator change, and the two types of phase signals output by the sync-signal control unit.

Further, according to another aspect of the present invention, a vector detecting device comprises a first reference-potential generating unit that generates a first reference-potential; an input amplifier that receives an AC signal with a known frequency, amplifies or buffers, and outputs the AC signal; a phase sensitivity detector that detects a phase sensitivity of the amplified or buffered AC signal output by the input amplifier using the first reference-potential as a reference; a second reference-potential generating unit that generates a second reference-potential higher than the first reference-potential; a charge/discharge change-over switch that switches the connection between the first reference-potential and the second reference-potential and the AC signal of which the phase sensitivity has been detected by the phase-sensitivity detector; an integrator that integrates the AC signal of which the phase sensitivity has been detected, from the charge/discharge change-over switch, and outputs the integrated potential; a third reference-potential generating unit that generates a third reference-potential lower than the first reference-potential; a comparator that outputs signals at levels varying depending on whether the potential output and integrated by the integrator is higher than the third reference-potential or lower than the third reference-potential; an integrating-time timer unit that counts an outputting time of the potential integrated by the integrator; a sync-signal control unit that outputs to the phase-sensitivity detector two types of phase signals synchronous with the AC signal with a constant phase thereof; a charge/discharge control unit that outputs to the charge/discharge change-over switch a control signal for switching the connection between the first reference-potential and the second reference-potential and the AC signal of which the phase sensitivity has been detected, to discharge the integrator until the time counted by the integrating-time timer unit reaches a predetermined time from a discharging start time and, thereafter, a control signal for switching the connection between the first reference-potential and the second reference-potential and the AC signal of which the phase sensitivity has been detected to charge the integrator until the levels of the signals output by the comparator change; and a vector-detecting-information calculating unit that outputs to the charge/discharge change-over switch vector detecting information of the AC signal received by the input amplifier on the basis of a time which reaches the predetermined time from the discharging start time counted by the integrating-time timer unit when the charge/discharge control unit outputs to the charge/discharge change-over switch the control signal for switching the connection to discharge the integrator, the time counted by the integrating-time timer unit when the charge/discharge control unit outputs the control signal for switching the connection to charge the integrator when the levels of the signals output by the comparator, and the two types of phase signals output by the sync-signal control unit.

Furthermore, according to another aspect of the present invention, a living-body complex impedance measuring apparatus comprises an AC constant-current signal generating unit that generates a sinusoidal AC constant-current signal with a known frequency; a reference impedance that is connected to the living body serially or in parallel therewith, to which the sinusoidal AC constant-current signal flows; a selector that switches a connection via the living body or the reference impedance; a first reference-potential generating unit that generates a first reference-potential; an input amplifier that receives the sinusoidal AC constant-current signal via the selector, amplifies or buffers, and outputs the sinusoidal AC constant-current signal; a phase-sensitivity detector that detects a phase sensitivity of the amplified or buffered sinusoidal AC constant-current signal using the first reference-potential as a reference; a second reference-potential generating unit that generates a second reference-potential lower than the first reference-potential; a charge/discharge change-over switch that switches the connection between the first reference-potential and the second reference-potential and the sinusoidal AC constant-current signal of which the phase sensitivity has been detected; an integrator that integrates the sinusoidal AC constant-current signal of which the phase sensitivity has been detected from the charge/discharge change-over switch, and outputs the integrated potential; a third reference-potential generating unit that generates a third reference-potential higher than the first reference-potential; a comparator that outputs signals at levels varying depending on whether the potential output and integrated by the integrator is higher than the third reference-potential or lower than the third reference-potential; an integrating-time timer unit that counts an outputting time of the potential integrated by the integrator; a sync-signal control unit that outputs two types of phase signals synchronous with a sinusoidal AC constant-current signal with a constant phase thereof to the phase-sensitivity detector; a charge/discharge control unit that outputs to the charge/discharge change-over switch a control signal for switching the connection between the first reference-potential and the second reference-potential and the sinusoidal AC constant-current signal of which the phase sensitivity has been detected, to charge the integrator until the time counted by the integrating-time timer unit reaches a predetermined time from a charging start time and, thereafter, a control signal for switching the connection between the first reference-potential and the second reference-potential and the sinusoidal AC constant-current signal of which the phase sensitivity has been detected, to discharge the integrator until the levels of the signals output by the comparator change; a vector-detecting information calculating unit that calculates the vector detecting information of the sinusoidal AC constant-current signal received by the input amplifier on the basis of the time which reaches the predetermined time from the charging start time counted by the integrating-time timer unit when the charge/discharge control unit outputs to the charge/discharge change-over switch the control signal for switching the connection to charge the integrator, the time counted by the integrating-time timer unit when charge/discharge control unit outputs to the charge/discharge change-over switch the control signal for switching the connection to discharge the integrator until the levels of the signals output by the comparator change, and the two types of phase signals output by the sync-signal control unit; and a living-body impedance calculating unit that calculates living-body impedance on the basis of the vector detecting information calculated by the vector-detecting-information calculating unit.

In addition, according to another aspect of the present invention, a living-body complex impedance measuring apparatus comprises an AC constant-current signal generating unit that generates a sinusoidal AC constant-current signal with a known frequency; a reference impedance that is connected to the living body serially or in parallel therewith, to which the sinusoidal AC constant-current signal flows; a selector that switches the connection via the living body or the reference impedance; a first reference-potential generating unit that generates a first reference-potential; an input amplifier that receives the sinusoidal AC constant-current signal via the selector, amplifies or buffers, and outputs the sinusoidal AC constant-current signal; a phase-sensitivity detector that detects a phase sensitivity of the amplified or buffered sinusoidal AC constant-current signal using the first reference-potential as a reference; a second reference-potential generating unit that generates a second reference-potential higher than the first reference-potential; a charge/discharge change-over switch that switches the connection between the first reference-potential and the second reference-potential and the sinusoidal AC constant-current signal of which the phase sensitivity has been detected by the phase-sensitivity detector; an integrator that integrates the sinusoidal AC constant-current signal of which the phase sensitivity has been detected from the charge/discharge change-over switch, and outputs the integrated potential; a third reference-potential generating unit that generates a third reference-potential lower than the first reference-potential; a comparator that outputs signals at levels varying depending on whether the potential integrated and output by the integrator is higher than the third reference-potential or lower than the third reference-potential; an integrating-time timer unit that counts an outputting time of the potential integrated by the integrator; a sync-signal control unit that outputs two types of phase signals synchronous with the sinusoidal AC constant-current signal with a constant phase thereof to the phase-sensitivity detector; a charge/discharge control unit that outputs to the charge/discharge change-over switch a control signal for switching the connection between the first reference-potential and the second reference-potential and the sinusoidal AC constant-current signal of which the phase sensitivity has been detected, to discharge the integrator until the time counted by the integrating-time timer unit reaches a predetermined time from a discharging start time and, thereafter, a control signal for switching the connection between the first reference-potential and the second reference-potential and the sinusoidal AC constant-current signal of which the phase sensitivity is detected, to charge the integrator until the levels of the signals output by the comparator change; a vector-detecting-information calculating unit that calculates the vector detecting information of the sinusoidal AC constant-current signal received by the input amplifier on the basis of the time which reaches the predetermined time from the discharging start time counted by the integrating-time timer unit when the charge/discharge control unit outputs to the charge/discharge change-over switch the control signal for switching the connection to discharge the integrator, the time counted by the integrating-time timer unit when the charge/discharge control unit outputs to the charge/discharge change-over switch the control signal for switching the connection to charge the integrator when the levels of the signals output by the comparator change and the two types of phase signals output by the sync-signal control unit; and a living-body impedance calculating unit that calculates living-body impedance on the basis of the vector detecting information calculated by the vector-detecting-information calculating unit.

In the vector detecting device according to the present invention, vector detecting information of an AC signal with a known frequency can be obtained by directly A/D converting the AC signal of which a phase sensitivity is detected by the phase-sensitivity detector. The number of parts can be reduced, the generation of an offset voltage can be prevented, and a target output can be simultaneously detected.

Further, in the living-body complex impedance measuring apparatus having a vector detecting device, vector detecting information of an AC signal with a known frequency can be obtained by directly A/D converting the AC signal of which a phase sensitivity is detected by the phase-sensitivity detector. The number of parts can be reduced, the generation of an offset voltage can be prevented, and it is possible to obtain living-body impedance for which a vector of a target output is detected with the prevention of generation of an offset voltage.

DESCRIPTION OF THE PREFERRED EMBODIMENT

Hereinbelow, a description is given of a vector detecting device according to an embodiment of the present invention with a block diagram shown in FIG. 1 and a flowchart shown in FIG. 2.

Figure 1:
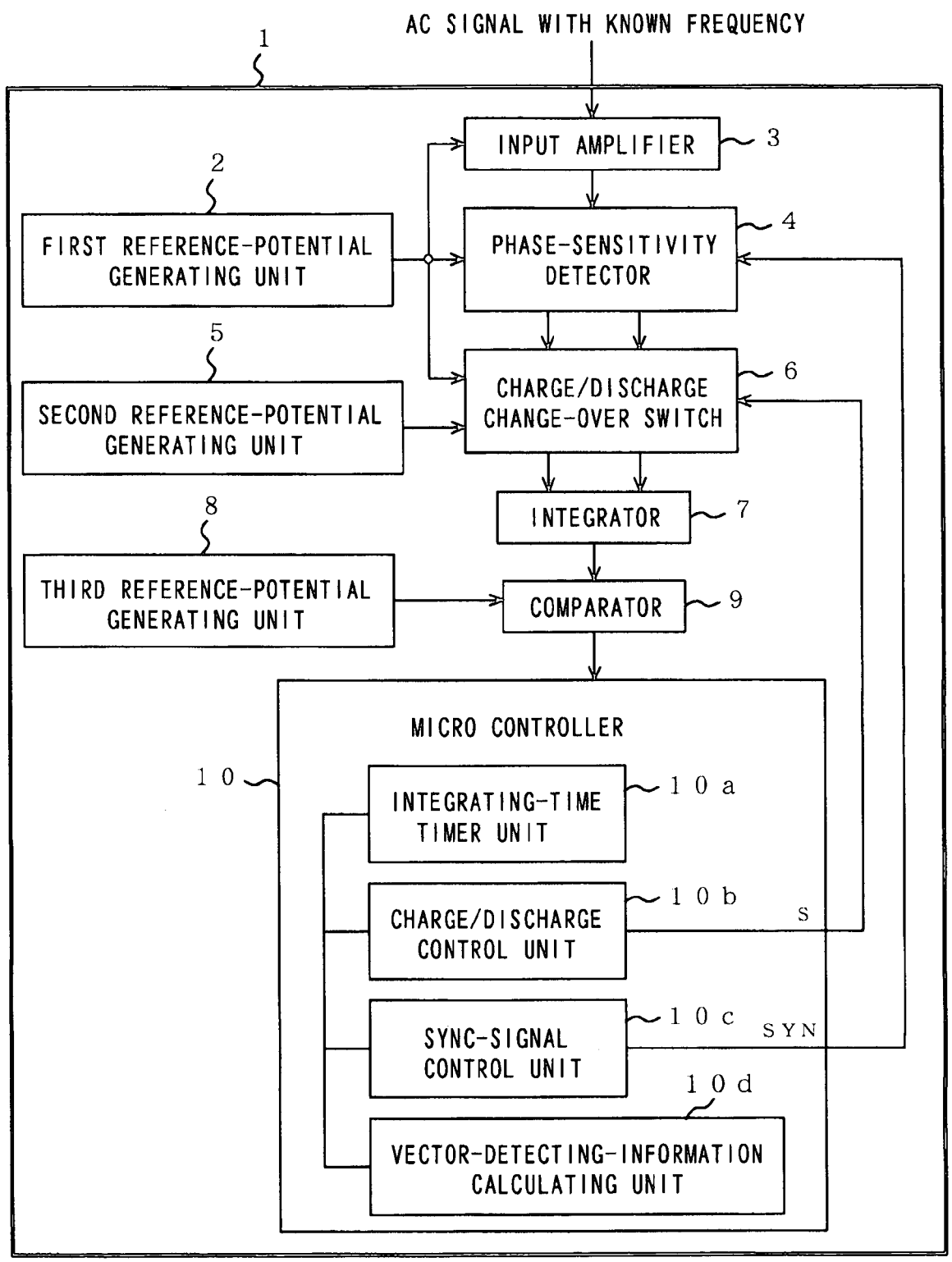
FIG. 1 is a block diagram showing the structure of a vector detecting device according to the present invention.
Figure 2:
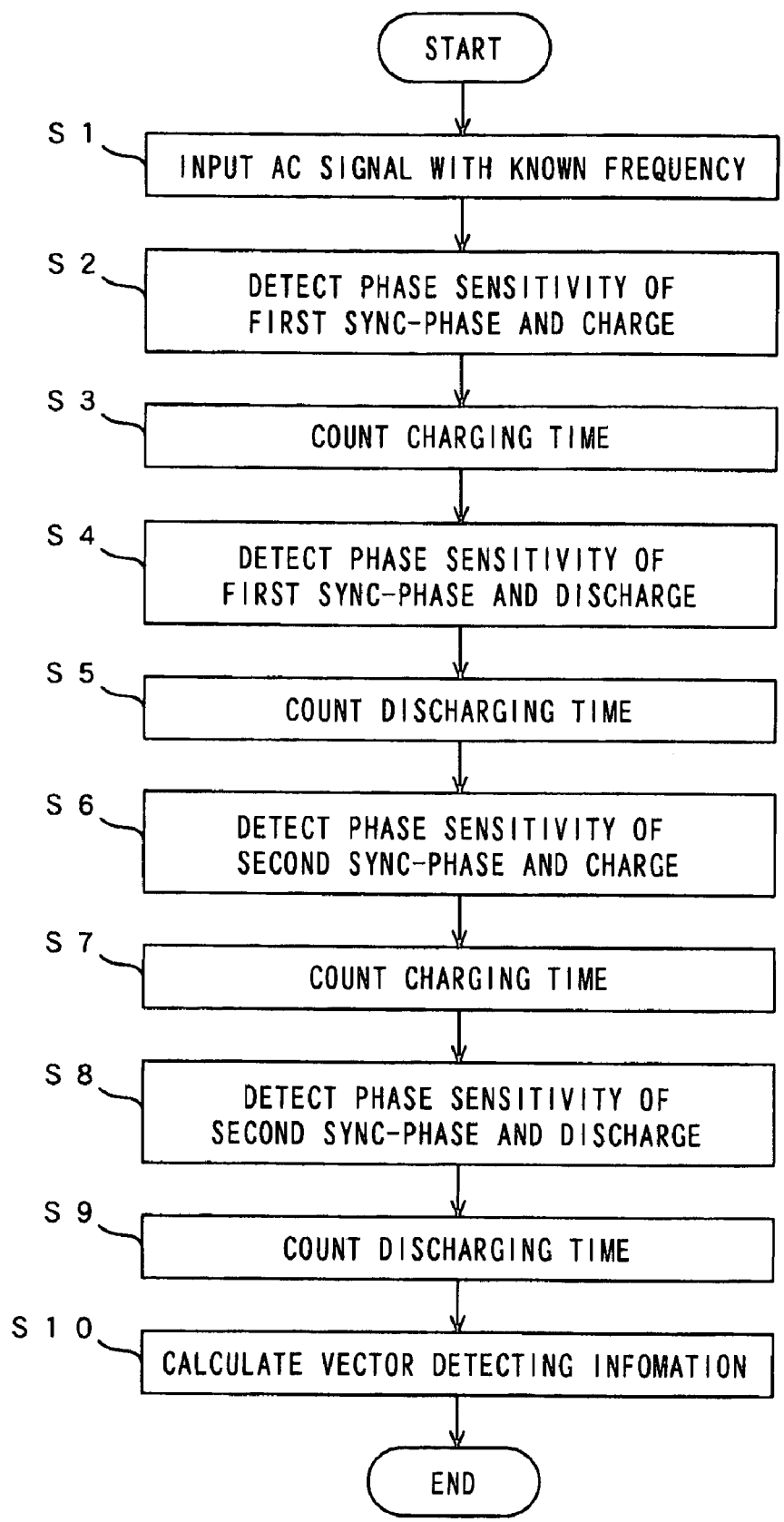
FIG. 2 is a flowchart showing the sequence of operating processing of a vector detecting device according to an embodiment of the present invention.

Referring to FIG. 1, a vector detecting device 1 according to the present invention comprises: a first reference-potential generating unit 2; an input amplifier 3; a phase-sensitivity detector 4; a second reference-potential generating unit 5; a charge/discharge change-over switch 6; an integrator 7; a third reference-potential generating unit 8; a comparator 9; and a micro controller 10 (including an integrating-time timer unit 10a, a charge/discharge control unit 10b, a sync-signal control unit 10c, and a vector-detecting-information calculating unit 10d).

The first reference-potential generating unit 2 generates a first reference-potential to the input amplifier 3, the phase-sensitivity detector 4, and the charge/discharge change-over switch 6.

The input amplifier 3 receives an AC signal with a known frequency, amplifies (positive-amplifies and negative-amplifies) or buffers, and outputs the AC signal with the known frequency (e.g., impedance-converts an input/output).

The phase-sensitivity detector 4 detects a phase sensitivity of the AC signal with the known frequency that is amplified and is output by the input amplifier 3 using the first reference-potential as a reference.

The second reference-potential generating unit 5 generates a second reference-potential lower than the first reference-potential that is generated by the first reference-potential generating unit 2.

The charge/discharge change-over switch 6 switches the connection of the first reference-potential generated by the first reference-potential generating unit 2, the second reference-potential generated by the second reference-potential generating unit 5, and the AC signal of which the phase sensitivity is detected by the phase-sensitivity detector 4.

The integrator 7 integrates the AC signal of which the phase sensitivity from the charge/discharge change-over switch 6 is detected, and outputs the integrated potential.

The third reference-potential generating unit 8 generates a third reference-potential higher than the first reference-potential generated by the first reference-potential generating unit 2. Preferably, the third reference-potential cannot be saturated in the integration of the integrator 7 and has an output amplitude which is as large as possible.

The integrating-time timer unit 10a counts an integrating time of the potential integrated by the integrator 7, including a charging time that reaches a predetermined time from a charging start time and a discharging time that reaches a time when the third reference-potential matches the potential integrated by the integrator from a discharging start time.

The sync-signal control unit 10c outputs, to the phase-sensitivity detector 4, two types of phase signals (preferably, with a 90 degree phase shift) which are synchronized with the AC signal with the known frequency with a predetermined phase thereof.

The charge/discharge control unit 10b outputs, to the charge/discharge change-over switch 6, a control signal for switching the connection between the first reference-potential and the second reference-potential and the AC signal of which the phase sensitivity has been detected to the charging operation until the time counted by the integrating-time timer unit 10a reaches the predetermined time from the charging start time. Thereafter, the charge/discharge control unit 10b further outputs, to the charge/discharge change-over switch 6, a control signal for switching the connection between the first reference-potential and the second reference-potential and the AC signal of which the phase sensitivity has been detected to the discharging operation until the levels of the signals output by the comparator 9 change.

The vector-detecting-information calculating unit 10d calculates vector detecting information of the AC signal having the known frequency received by the input amplifier 3, on the basis of the time (charging time) that reaches the predetermined time from the charging start time counted by the integrating-time timer unit 10a when the charge/discharge control unit 10b outputs, to the charge/discharge change-over switch 6, the control signal for switching the connection to perform the charging operation, the time (discharging time) counted by the integrating-time timer unit 10a when the charge/discharge control unit 10b outputs, to the charge/discharge change-over switch 6, the control signal for switching the connection to perform the discharging operation until the level of the signal output by the comparator 9 changes, and the two types of the phase signals output by the sync-signal control unit 10c.

Subsequently, the vector detecting device 1 according to the present invention performs an operation for obtaining the vector detecting information in accordance with the flow shown in FIG. 2.

The input amplifier 3 receives an AC signal (A sin(ft+θ) where reference symbol A denotes an amplitude, reference symbol f denotes a frequency, reference symbol t denotes a time, and reference symbol θ denotes a phase) having a known frequency, amplifies (positive-amplifies and negative-amplifies) or buffers and outputs the AC signal with the known frequency (e.g., impedance-converts an input/output). Herein, note that the input amplifier 3 amplifies (positive-amplifies) and outputs the signal on the basis of the first reference-potential, as a reference, generated by the first reference-potential generating unit 2 (in step S1).

Subsequently, the sync-signal control unit 10c outputs a phase (e.g., a first sync-phase (=0 degree)) synchronized with the AC signal having the known frequency, amplified and output by the input amplifier 3, with a predetermined phase to the phase-sensitivity detector 4. The charge/discharge control unit 10b outputs, to the charge/discharge change-over switch 6, a signal (e.g., S=Low) for switching the connection to perform the charging operation. Then, the integrator 7 starts the charging operation in accordance with an output (X-Y) relative to the first sync-phase from the phase-sensitivity detector 4 (in step S2).

The integrating-time timer unit 10a counts a predetermined charging time (tm). Then, the integrator 7 performs the charging operation until the time reaches the predetermined charging time (tm) (in step S3).

The charge/discharge control unit 10b outputs, to the charge/discharge change-over switch 6, a signal (e.g., S=Hi) for switching the connection to perform the discharging operation. Then, the integrator 7 starts the discharging operation in accordance with [(the first reference potential)−(second reference-potential)]. The discharging operation is performed, until the output potential of the integrator 7 matches the third reference-potential generated by the third reference-potential generating unit 8, and then the level of the signal output by the comparator 9 is changed (in step S4).

The integrating-time timer unit 10a counts a time (tend−tst) from the discharging start time (tst) to a time (tend) at which the level of the signal output by the comparator 9 is changed. The integrator 7 thus performs the discharging operation from the time (tst) to the time (tend) at which the level of the signal output from the comparator 9 is changed (in step S5).

The sync-signal control unit 10c outputs, to the phase-sensitivity detector 4, a phase (e.g., a second sync-phase (=90 degrees)) synchronous with the AC signal having the known frequency, amplified and output by the input amplifier 3. The charge/discharge control unit 10b outputs, to the charge/discharge change-over switch 6, a signal (e.g., S=Low) for switching the connection to perform the charging operation. Then, the integrator 7 starts the charging operation in accordance with an output (X-Y) relative to the second sync-phase from the phase-sensitivity detector 4 (in step S6).

The integrating-time timer unit 10a counts a predetermined charging time (tm). Then, the integrator 7 performs the charging operation until the time reaches the predetermined charging time (tm) (in step S7).

The charge/discharge control unit 10b outputs, to the charge/discharge change-over switch 6, a signal (e.g., S=Hi) for switching the connection to perform the discharging operation. Subsequently, the integrator 7 starts the discharging operation of the integrator 7 in accordance with [(the first reference-potential)−(second reference-potential)]. The discharging operation is performed until the output potential of the integrator 7 matches the third reference-potential generated by the third reference-potential generating unit 8 and the levels of the signals output by the comparator 9 change (in step S8).

The integrating-time timer unit 10a counts a discharging time (tend-tst) from a discharging start time (tst) to a time (tend) at which the levels of the signals output by the comparator 9 change. The integrator 7 performs the discharging operation from the discharging start time (tst) to the time (tend) at which the levels of the signals output by the comparator 9 are output (in step S9).

Subsequently, the vector-detecting-information calculating unit 10d calculates the vector detecting information (A cos θ) on the basis of the charging time (tm) and the discharging time (tend−tst) in the charging operation and the discharging operation of the first sync-phase by using the following Expression (1) where reference symbol a denotes a constant specific to a device, reference symbol A denotes an amplitude, and reference symbol θ denotes a phase.

$$\alpha(tend-tst)/tm = A \cos \theta \qquad (1)$$

Subsequently, the vector-detecting-information calculating unit 10d calculates vector detecting information (A sin θ) on the basis of the charging time (tm) and the discharging time (tend-tst) in the charging operation and the discharging operation of the second sync-phase by using the following Expression (2) where reference symbol a denotes a constant specific to a device, reference symbol A denotes an amplitude, and reference symbol θ denotes a phase.

$$\alpha(tend-tst)/tm = A \sin \theta \qquad (2)$$

The above-mentioned operation is executed, and the processing for detecting the vector ends.

In the vector detecting device 1 having the above-described structure, the vector detecting information of the AC signal having the known frequency can be obtained by directly A/D converting the AC signal of which the phase sensitivity is detected by the phase-sensitivity detector 4. The number of parts can be reduced, the generation of an offset voltage can be prevented, and a target output can be simultaneously detected.

In the above-mentioned vector detecting device 1, the vector detecting information of the AC signal having the known frequency is obtained on the basis of the time that reaches the predetermined time from the charging start time point, counted by the integrating-time timer unit 10a, when the charge/discharge control unit 10b outputs, to the charge/discharge change-over switch 6, the control signal for switching the connection to charge the integrator 7, the time counted by the integrating-time timer unit 10a when the charge/discharge control unit 10b outputs, to the charge/discharge change-over switch 6, the control signal for switching the connection to discharge the integrator 7 until the levels of the signals output by the comparator 9 change, and the two types of phase signals output by the sync-signal control unit 10c. Alternatively, in the above-mentioned vector detecting device 1, the vector detecting information of the AC signal having the known frequency can be obtained on the basis of the time that reaches a predetermined time from the discharging start time point, counted by the integrating-time timer unit 10a, when the charge/discharge control unit 10b outputs, to the charge/discharge change-over switch 6, the control signal for switching the connection to discharge the integrator 7, the time counted by the integrating-time timer unit 10a when the charge/discharge control unit 10b outputs, to the charge/discharge change-over switch 6, the control signal for switching the connection to charge the integrator 7 until the levels of the signals output by the comparator 9 change, and the two types of phase signals output by the sync-signal control unit 10c.

In this case, the second reference-potential generating unit 5 can generate a second reference-potential higher than the first reference-potential that is generated by the first reference-potential generating unit 2. The third reference-potential generating unit 8 can generate the third reference-potential lower than the first reference-potential generated by the first reference-potential generating unit 2. The integrating-time timer unit 10 can count the outputting times [including the (discharging time) from the discharging start time to a predetermined time and the (charging time) from the charging start time to the time when the third reference-potential is matched] of the potentials integrated by the integrator 7. The charge/discharge control unit 10b can output, to the charge/discharge change-over switch 6, the control signal for switching the connection between the first reference-potential and the second reference-potential and the AC signal of which the phase sensitivity is detected to discharge the integrator 7 until the time counted by the integrating-time timer unit 10a reaches a predetermined time from the discharging start time. Thereafter, the charge/discharge control unit 10b can further output, to the charge/discharge change-over switch 6, the control signal for switching the connection between the first reference-potential and the second reference-potential and the AC signal of which the phase sensitivity is detected to charge the integrator 7 until the levels of the signals output by the comparator 9 change. The vector-detecting-information calculating unit 10d can calculate the vector detecting information of the AC signal with the known frequency, input by the input amplifier 3, on the basis of the time (discharging time) to a predetermined time from the discharging start time, counted by the integrating-time timer unit 10a, when the charge/discharge control unit 10b outputs, to the charge/discharge change-over switch 6, the control signal for switching the connection to discharge the integrator 7, the time (charging time) counted by the integrating-time timer unit 10a when the charge/discharge control unit 10b outputs, to the charge/discharge change-over switch 6, the control signal for switching the connection to charge the integrator 7 until the levels of the signals output by the comparator 9 change, and the two types of phase signals output by the sync-signal control unit 10c.

Note that the above-stated vector detecting device can be used as a part of another apparatus. Next, as an example thereof, a description is given of a living-body complex impedance measuring apparatus having the above-mentioned vector detecting device.

Figure 3:
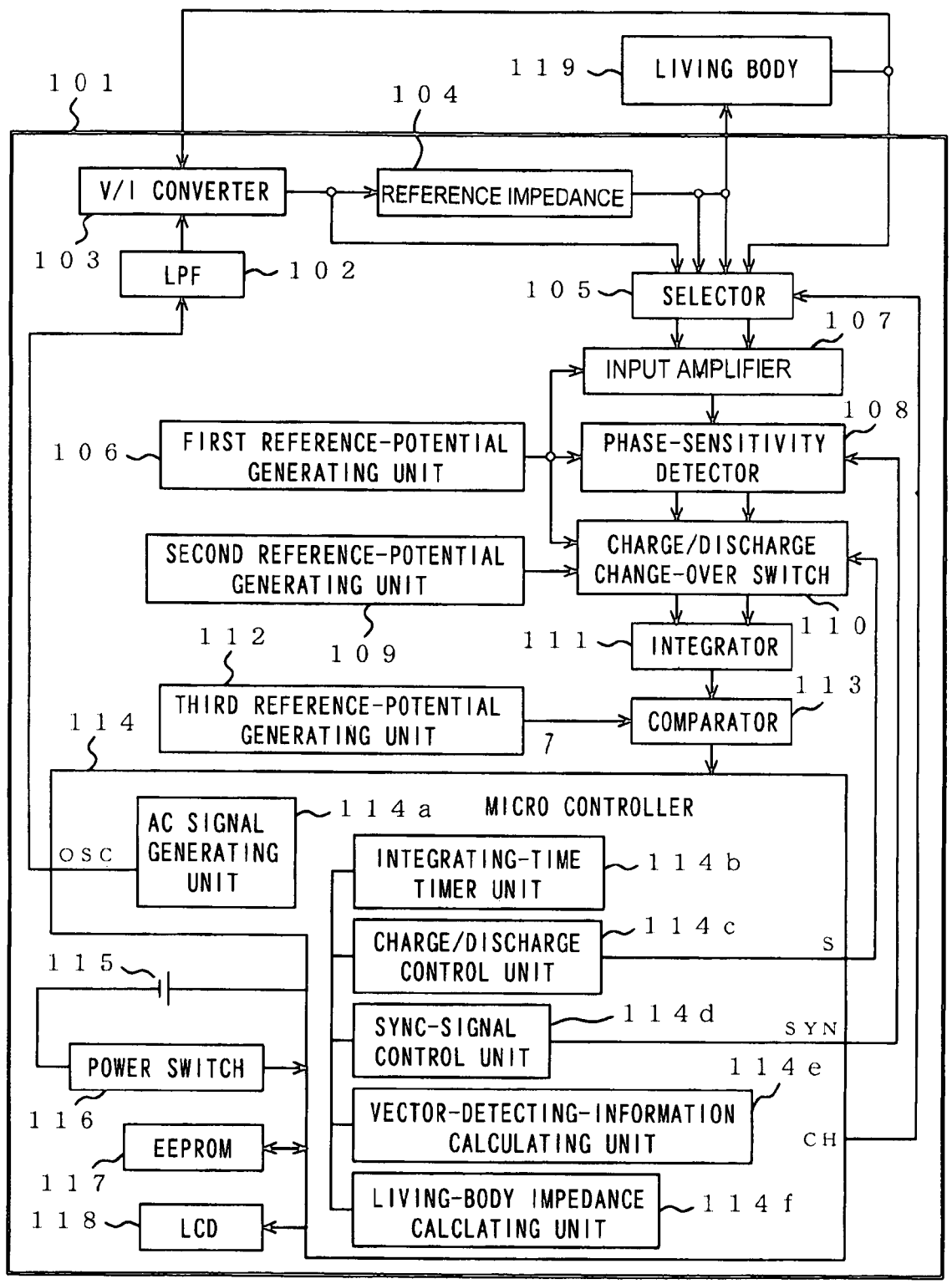
FIG. 3 is a block diagram showing the structure of a living-body complex impedance measuring apparatus having a vector detecting device, according to an embodiment of the present invention.
Figure 4:
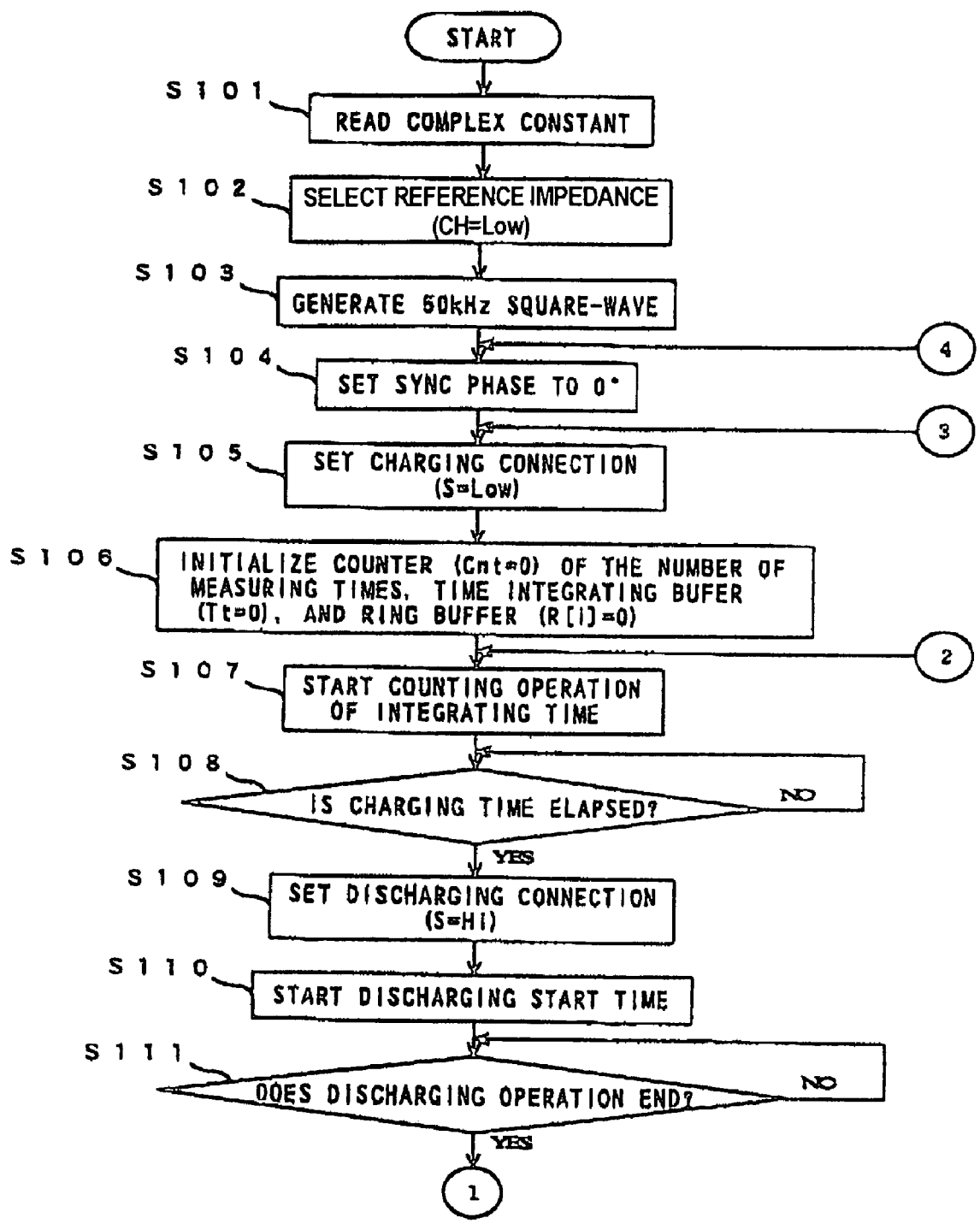
FIG. 4 is a flowchart showing the first part of a sequence of operating processing of a living-body complex impedance measuring apparatus having a vector detecting device according to an embodiment of the present invention.
Figure 5:
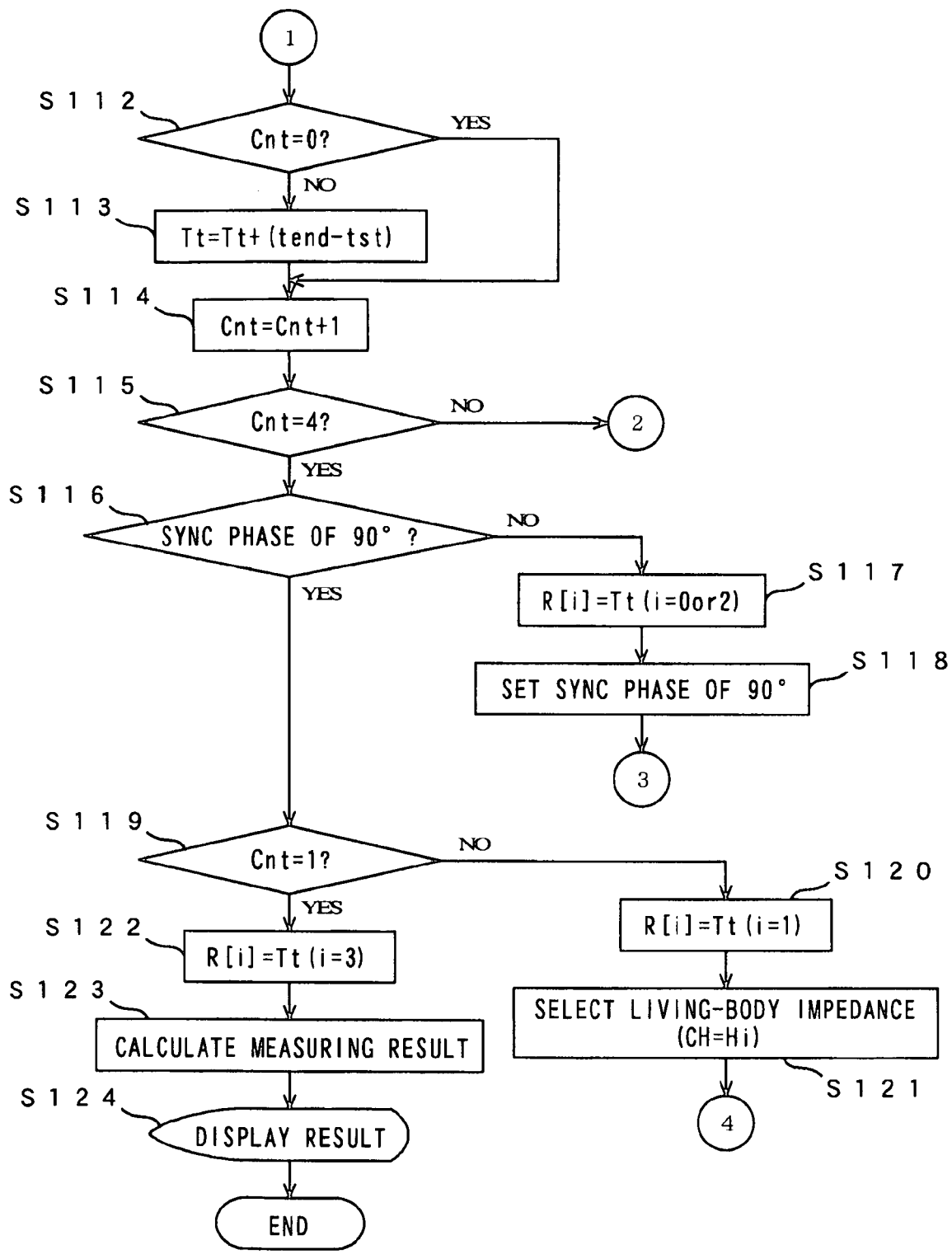
FIG. 5 is a flowchart showing the second part of a sequence of operating processing of a living-body complex impedance measuring apparatus having a vector detecting device according to an embodiment of the present invention.
Figure 6:
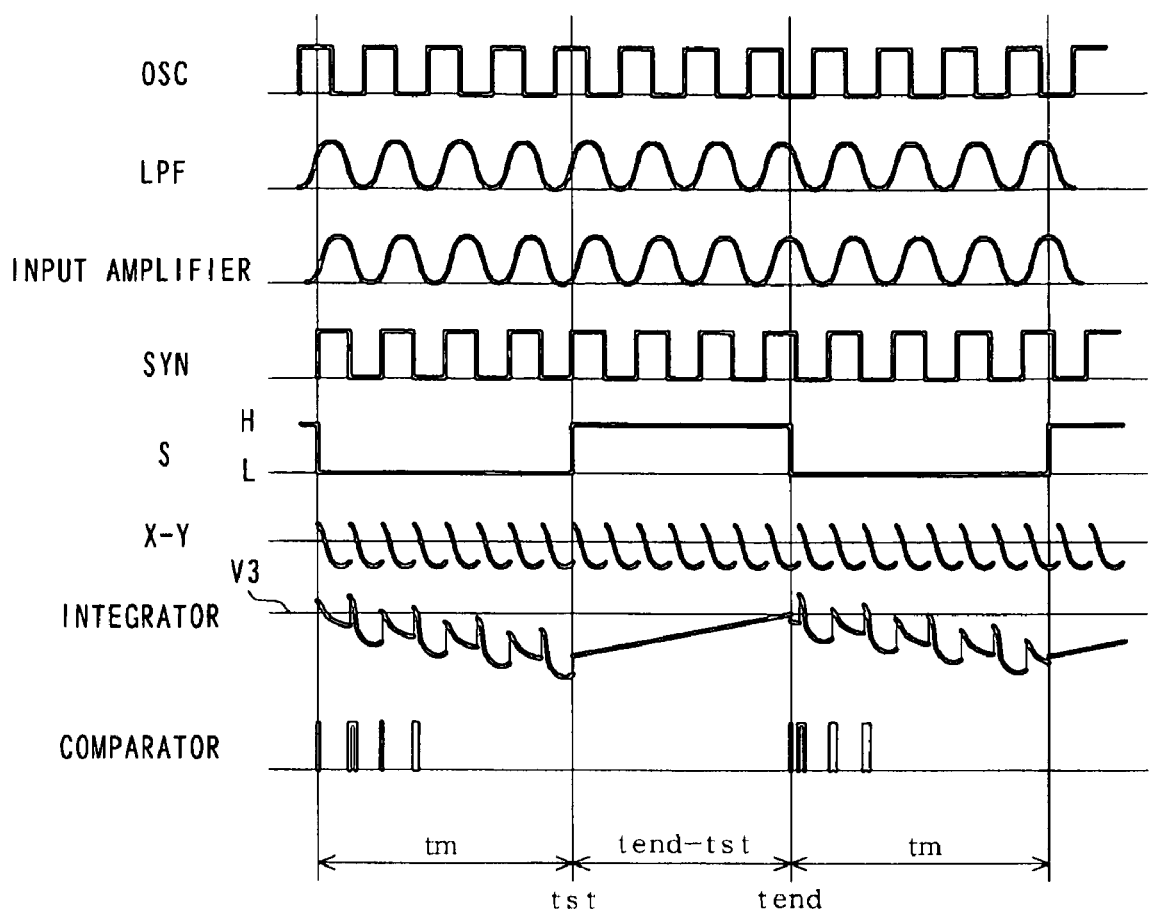
FIG. 6 is a waveform diagram of units in a living-body complex impedance measuring apparatus having a vector detecting device according to an embodiment of the present invention.

A description is given of the living-body complex impedance measuring apparatus having a vector detecting device according to the present invention with reference to a block diagram shown in FIG. 3, flowcharts shown in FIGS. 4 and 5, and a waveform diagram shown in FIG. 6.

First, referring to FIG. 3, a living-body complex impedance measuring apparatus 101 having a vector detecting device according to the present invention comprises: an LPF (Low-Pass Filter) 102; a V/I converter 103; a reference impedance 104; a selector 105; a first reference-potential generating unit 106; an input amplifier 107; a phase-sensitivity detector 108; a second reference-potential generating unit 109; a charge/discharge change-over switch 110; an integrator 111; a third reference-potential generating unit 112; a comparator 113; a micro controller 114 (including an AC signal generating unit 114a, an integrating-time timer unit 114b, a charge/discharge control unit 114c, a sync-signal control unit 114d, a vector-detecting-information calculating unit 114e, and a living-body impedance calculating unit 114f); a power supply 115; a power switch 116; an EEPROM (Electronically Erasable and Programmable Read Only Memory) 117; and an LCD (Liquid Crystal Display) 118.

Note that the inventive vector detecting device comprises the first reference-potential generating unit 106; the input amplifier 107; the phase-sensitivity detector 108; the second reference-potential generating unit 109; the charge/discharge change-over switch 110; the integrator 111; the third reference-potential generating unit 112; the comparator 113; and the micro controller 114 (including the integrating-time timer unit 114b, the charge/discharge control unit 114c, the sync-signal control unit 114d, and the vector-detecting-information calculating unit 114e).

Further, an AC constant-current signal generating unit generates a sinusoidal AC constant-current signal having a known frequency and further comprises the AC signal generating unit 114a, the LPF 102, and the V/I converter 103.

The AC signal generating unit 114a outputs a 50 kHz square-wave (waveform OSC shown in FIG. 6).

The LPF 102 converts and outputs the 50 kHz square-wave output by the AC signal generating unit 114a to a 50 kHz sinusoidal wave (waveform LPF shown in FIG. 6).

The V/I converter 103 converts and outputs the 50 kHz sinusoidal wave converted and output by the LPF 102 to 50 kHz constant-current.

The reference impedance 104 is connected to the living body 119 serially or in parallel therewith (serial connection in the example, as shown in FIG. 3), thereby flowing the 50 kHz constant-current output from the V/I converter 103. Note that the reference impedance 104 corrects the influence from disturbances, such as the change of constant current due to the temperature change of an environment.

The selector 105 switches the connection via the reference impedance 104 or the living body 119 under the control operation of the micro controller 114.

The first reference-potential generating unit 106 generates a first reference-potential (preferably, potential at the middle point of a power voltage) to the input amplifier 107, the phase-sensitivity detector 108, and the charge/discharge change-over switch 110.

The input amplifier 107 inputs the 50 kHz constant-current flowing via the reference impedance 104 or the living body, and amplifies and outputs the 50 kHz constant-current on the basis of the first reference-potential, as a reference, generated by the first reference-potential generating unit 106 (waveform of input amplifier shown in FIG. 6).

The phase-sensitivity detector 108 detects the phase sensitivity (X, Y) of the 50 kHz constant-current amplified and output by the input amplifier 107 using the first reference-potential as a reference, generated by the first reference-potential generating unit 106 on the basis of the square wave (waveform SYN shown in FIG. 6) from the sync-signal control unit 114*d*.

The second reference-potential generating unit 109 generates a second reference-potential (e.g., potential corresponding to ⅓ of the power voltage) lower than the first reference-potential generated by the first reference-potential generating unit 106.

The charge/discharge change-over switch 110 switches the connection on the basis of the Low signal (i.e., the potential of signal S=Low shown in FIG. 6) from the charge/discharge control unit 114*c* so as to output signals of [(the AC signal of which the phase sensitivity has been detected)−(the first reference-potential)] and [(the first reference-potential)−(the AC signal of which the phase sensitivity has been detected)] (i.e., waveform X-Y shown in FIG. 6) from the first reference-potential, the second reference-potential, and the AC signal of which the phase sensitivity has been detected. Further, charge/discharge change-over switch 110 switches the connection on the basis of the Hi signal (i.e., potential of signal S=Hi shown in FIG. 6) from the charge/discharge control unit 114*c*, the first reference-potential, as a reference, the second reference-potential, and the AC signal of which the phase sensitivity has been detected so as to output a signal of [(the second reference-potential)−(the first reference-potential)] (constant).

The integrator 111 outputs the integrated potential (i.e., waveform of the integrator shown in FIG. 6) on the basis of the signal (the AC signal of which the phase sensitivity has been detected) output from the charge/discharge change-over switch 110.

The third reference-potential generating unit 112 generates a third reference-potential (e.g., a potential of ⅔ of the power voltage) higher than the first reference-potential generated by the first reference-potential generating unit 106.

The comparator 113 outputs signals (waveforms of the comparator shown in FIG. 6) of varying levels depending on whether the potential output and integrated by integrator 111 is higher than the third reference-potential generated by the third reference-potential generating unit 112 or lower than the third reference-potential.

The integrating-time timer unit 114*b* counts an integrating time (the time tm that reaches a predetermined time from a predetermined charging start time) and a discharging time (the time (tend-tst) from a time when the potential is S=Hi to a time when the potential integrated by the integrator 111 reaches the third reference-potential).

The sync-signal control unit 114*d* outputs, to the phase-sensitivity detector 108, two types of phase signals; e.g., with phases shifted by 0 to −45 degrees corresponding to a phase delayed angle specific to a system of the apparatus with respect to a phase of the 50 kHz square-wave generated by the AC signal generating unit 114*a*. In one embodiment, one phase signal has a delayed angle of 0 degrees, a phase delayed by 90 to 45 degrees from the phase of the 50 kHz square-wave generated by the AC signal generating unit 114*a*, and another phase signal has a delay angle of 90 degrees, a phase delayed by 90 degrees from the phase delayed by 90 to 45 degrees.

The charge/discharge control unit 114*c* outputs, to the charge/discharge change-over switch 110, the control signal (S=Low) for switching the connection between the first reference-potential and the second reference-potential and the AC signal of which the phase sensitivity has been detected to charge the integrator 111 for the charging time (a time of n/2 time of a period of the signal generated by the AC signal generating unit 114 or the sync-signal control unit 114*d*). Thereafter, the charge/discharge control unit 114*c* further outputs, to the charge/discharge change-over switch 110, the control signal (S=Hi) for switching the connection between the first reference-potential and the second reference-potential and the AC signal of which the phase sensitivity has been detected to discharge the integrator 111 until the level (waveform of the comparator shown in FIG. 6) of the signal output by the comparator 1113 is changed.

The vector-detecting-information calculating unit 114*d* calculates the vector detecting information of the 50 kHz constant-current, input by the input amplifier 107, on the basis of the time (charging time) tm that reaches a predetermined time from the charging start time counted by the timer unit when the charge/discharge control unit 114*c* outputs, to the charge/discharge change-over switch 110, the control signal for switching the connection to charge the integrator 111, the time (discharging time) tend-tst counted by the integrating-time timer unit 114*b* when the charge/discharge control unit 114*c* outputs, to the charge/discharge change-over switch 110, the control signal for switching the connection to discharge the integrator 111 until the level of the signal output by the comparator 113 is changed, and the phase signals of 0 and 90 degrees output by the sync-signal control unit 114*d*.

The living-body impedance calculating unit 114*e* calculates living-body impedance on the basis of the vector detecting information calculated by the vector-detecting-information calculating unit 114*d*.

The power supply 115 supplies power to the components of the electronic system.

The power switch 116 switches the supply or stop of the power to the components of the electronic system from the power supply 115.

The EEPROM 117 stores information relating to the charging time and discharging time.

The LCD 118 displays various information including a measuring result and an input index.

Next, a description of how the living-body complex impedance measuring apparatus 101 having a vector detecting device according to the present invention operates will be given with reference to the flowcharts in FIGS. 4 and 5.

First, the power switch 116 is switched on. Then, the power supply 115 supplies the power to the components of the electronic system. Complex constants c and b stored in advance in the EEPROM 117 are read (in step S101).

Subsequently, the selector 105 is switched to the connection for measuring the reference impedance 104 on the basis of a signal of CH=Low from the micro controller 114 (in step S102).

The AC signal generating unit 114*a* outputs the 50 kHz square-wave (waveform OSC shown in FIG. 6), the LPF 102 converts the output signal into the 50 kHz sinusoidal wave, and the V/I converter 103 converts the signal into the 50 kHz constant-current. Subsequently, the converted 50 kHz constant-current flows to the reference impedance 104 and the living body 119 and returns to the V/I converter 103 (in step S103). In this case, the 50 kHz constant-current flowing to the reference impedance 104 and the 50 kHz constant-current living body 119 have the same phases. However, the voltage generated in the reference impedance 104 is different from the voltage generated in the living body 119, depending on absolutes and phase angles of the reference impedance 104 and the living-body impedance.

Subsequently, the sync-signal control unit 114*d* outputs the square waves (waveform SYN shown in FIG. 6) having a phase of 0 degrees synchronous with the phase-sensitivity detector 108 (in step S104). Note that the square waves having the synchronous phase of 0 degrees in this case have a phase different from the phase of the 50 kHz square-wave output by the AC signal generating unit 114*a*. Further, the input amplifier 107 outputs the same polarity as that of the LPF 102.

The charge/discharge control unit 114*c* outputs, to the charge/discharge change-over switch 10, a signal S (=Low) (square wave L of signal S shown in FIG. 6), for charging the integrating operation of the integrator 111 (in step S105). Thus, the phase-sensitivity detector 108 outputs a waveform X-Y (waveform X-Y shown in FIG. 6) which is equal to $\int f(\theta)\delta(\theta)d\theta = 4A\cos\phi$.

Subsequently, the micro controller 114 initializes a counter value Cnt of the number of measuring times for plural measurement, a value Tt of a time integrating buffer that integrates a double-integrating time, and values R[0] to R[4] of ring buffers for storing a measuring result with a sync phase of 0 degree in the charging operation, a measuring result with a sync phase of 0 degree in the discharging operation, a measuring result with a sync phase of 90 degrees in the charging operation, and a measuring result with a sync phase of 90 degrees in the discharging operation (Cnt=O, Tt=O, and R[0] to R[4]=0) (in step S106).

The integrating-time timer unit 114*b* starts the counting operation of the integrating time (in step S107).

Subsequently, the charge/discharge control unit 114*c* determines whether or not the counting result of the integrating-time timer unit 114*b* reaches the integrating time tm for predetermined charging operation (in step S108). When it is determined that the counting result does not reach the integrating time tm for predetermined charging operation (NO in step S108), the determination continues until the counting result reaches the integrating time tm. Herein, the integrating time tm uses 500 periods for the purpose of utilizing a time resolution of the integrating-time timer unit 114*b* as much as possible. That is, the integrating time tm is 500 s×(1/50 kHz)=10 ms. Further the integrating time tm is n/2 time of the period of the signal generated by the AC signal generating unit 114*a* (or the sync-signal control unit 114*d*) for the purpose of preventing the occurrence of errors.

On the other hand, when the counting result reaches the integrating time tm (10 ms) for predetermined charging operation (YES in step S108), the charge/discharge control unit 114*c* outputs a signal S (=Hi) (square wave H of signal S shown in FIG. 6) for charging the integrating operation of the integrator 111 to the charge/discharge change-over switch 110 (in step S109).

The charge/discharge control unit 114*c* stores the integrating start time tst for discharging operation of the integrating-time timer unit 114*b* (in step S110).

Subsequently, the charge/discharge control unit 114*c* determines whether or not the counting result reaches the integrating end time tend for discharging operation of the integrating-time timer unit 1114*b* (in step S111). When it is determined that the counting result does not reach the integrating end time tend for discharging operation (NO in step S111), the determination continues until the counting result reaches the integrating end time tend. Specifically, when the output potential of the integrator 111 is lower than a third reference-potential (V3 shown in FIG. 6) generated by the third reference-potential generating unit 112, the determination continues. On the other hand, when the counting result reaches the integrating end time tend for discharging operation (YES in step S111), the processing sequence advances to step S112.

Subsequently, it is determined whether or not the counter value Cnt of the number of measuring times in the micro controller 114 is 0 (in step S112). When the counter value Cnt of the number of measuring times is 0 (YES in step S112), the processing sequence advances to step S114. This processing is performed so as to prevent a case of obtaining no accurately measured data due to the switching of connection caused by the measurement of the reference impedance 104 or the living-body impedance and the influence from the change in sync phases.

On the other hand, when the counter value Cnt of the number of measuring times is not 0 (NO in step S112), the discharging time (tend-tst) currently-obtained is added to the value Tt of the time integrating buffer (in step S113).

The counter value Cnt of the number of measuring times in the micro controller 114 is incremented up by one (in step S114).

Subsequently, it is determined whether or not the counter value Cnt of the number of measuring times in the micro controller 114 is 4 (in step S115). When the counter value Cnt of the number of measuring times is not 4 (NO in step S115), the processing sequence returns to step S107 and then the processing is repeated. On the other hand, when the counter value Cnt of the number of measuring times is 4 (YES in step S115), the processing sequence advances to step S116.

It is determined whether or not the sync phase output to the phase-sensitivity detector 108 from the sync-signal control unit 114*d* is a square wave of 90 degrees (in step S116). When the sync phase is not the square wave of 90 degrees (NO in step S116), the value Tt of the time integrating buffer is stored in the value R[0] of the ring buffer (in step S117). Further, the sync signal control unit 114*d* outputs, to the phase-sensitivity detector 108, the square wave having the sync phase of 90 degrees (in step S118).

On the other hand, when the sync phase is the square wave of 90 degrees (YES in step S116), it is determined whether or not the counter value Cnt of the number of measuring times in the micro controller 114 is 1 (in step S119).

Subsequently, the counter value Cnt of the number of measuring times is not 1 (NO in step S119), the value Tt of the time integrating buffer is stored in the value R[1] of the ring buffer (in step S120), and the selector 105 is switched to the connection for measuring the living-body impedance on the basis of a signal CH (=Hi) from the micro controller 114 (in step S121). Subsequently, the processing sequence returns to step S105 and then the processing is repeated. Note that, in step S117 of the repetition of the processing, the value Tt of the time integrating buffer is stored in the value R[2] of the ring buffer.

On the other hand, when the counter value Cnt of the number of measuring times is 1 (YES in step S119), the value Tt of the time integrating buffer is stored in the value R[3] of the ring buffer (in step S122).

Subsequently, the vector-detecting-information calculating unit 114d substitutes the value R[0] of the ring buffer which is measured data of a cos element of the reference impedance 104, the value R[1] of the ring buffer which is measured data of a sin element of the reference impedance 104, the value R[2] of the ring buffer which is measured data of a cos element of the living-body impedance, and the value R[3] of the ring buffer which is measured data of a sin element of the living-body impedance for the following Expression (3) and Expression (4), thereby calculating the vector detecting information (complex impedance) (in step S1123).

$$Zr=\gamma(R[0]+jR[1]) \quad (3)$$

$$Zh=\gamma(R[2]+jR[3]) \quad (4)$$

Herein, reference symbol Zr denotes an impedance value of the reference impedance, reference symbol Zh denotes a value of living-body impedance, reference symbol $\gamma$ denotes a constant, and reference symbol j denotes a complex number. Further, the constant $\gamma$ is equal to P/Ic.

Note that Expression (3) and Expression (4) are derived as follows. When a constant charging time is designated by tm and a discharging time is designated by (tend-tst), an input voltage Vin is obtained by $\alpha$(tend−tst)/tm under a general expression of double integration where $\alpha$ denotes a constant specific to a device. In the above steps, the addition is respectively repeated three times for measurement of the cos element of the reference impedance 104, measurement of the sin element of the reference impedance 104, measurement of the cos element of the living-body impedance, and measurement of the sin element of the living-body impedance. As a consequence thereof, the input voltages Vin in the individual measurements are Vin[0]=$\alpha$R[0]/3tm, Vin[1]=$\alpha$R[1]/3tm, Vin[2]=$\alpha$R[2]/3tm, and Vin[3]=$\alpha$R[3]/3tm. These values include the cos element in the case of the sync phase of 0 degree and the sin element in the case of the sync phase of 90 degrees. Thus, $\alpha$ and 3tm are replaced with another constant $\beta$ specific to a device, thereby obtaining |Zr|·Ic·cos $\phi$r=$\beta$·R[0], |Zr|·Ic·sin $\phi$r=$\beta$·R[1], |Zh|·Ic·cos $\phi$h=$\beta$·R[2], and |Zh|·Ic·sin $\phi$h=$\beta$·R[3]. Subsequently, a value Ic of the 50 kHz constant-current output by the V/I converter 103 and the constant $\beta$ are replaced with another constant $\gamma$ specific to a device, thereby obtaining Expression (3) and Expression (4).

Further, the living-body impedance calculating unit 114e substitutes the vector detecting information (complex impedance Zr and Zh) calculated by the vector-detecting-information calculating unit 114d and the complex constants c and b read in step S101 for the following Expression (5), thereby calculating the living-body impedance (in step S123).

$$Zm=c \cdot Zm/Zr+b \quad (5)$$

Through the above-mentioned operating processing, the measuring processing of the living-body impedance of which the vector is detected ends.

In the living-body complex impedance measuring apparatus 101 having a vector detecting device with the above-described structure, the vector detecting information of the AC signal having the known frequency can be obtained by directly A/D converting the AC signal of which the phase sensitivity is detected by the phase-sensitivity detector 108. As a consequence thereof, it is possible to obtain a living-body impedance in which the vector of a target output is detected without generating an offset voltage.

Incidentally, in the above-mentioned living-body complex impedance measuring apparatus 101 having the inventive vector detecting device, the vector detecting information of the AC signal with the known frequency is obtained on the basis of the time that reaches a predetermined time from the charging start time counted by the integrating-time timer unit 114b when the charge/discharge control unit 114c outputs, to the charge/discharge change-over switch 110, the control signal for switching the connection to charge the integrator 111, the time counted by the integrating-time timer unit 114b when the charge/discharge control unit 114c outputs, to the charge/discharge change-over switch 110, the control signal for switching the connection to discharge the integrator 111 until the levels of the signals output by the comparator 113 change, and the two types of phase signals output by the sync-signal control unit 114d. Alternatively, the vector detecting information of the AC signal with the known frequency can be obtained on the basis of the time that reaches a predetermined time from the discharging start time counted by the integrating-time timer unit 114b when the charge/discharge control unit 114c outputs, to the charge/discharge change-over switch 110, the control signal for switching the connection to discharge the integrator 111, the time counted by the integrating-time timer unit 114b when the charge/discharge control unit 114c outputs, to the charge/discharge change-over switch 110, the control signal for switching the connection to charge the integrator 111 until the levels of the signals output by the comparator 113 change, and the two types of phase signals output by the sync-signal control unit 114d.

In this case, the second reference-potential generating unit 109 can generate a second reference-potential higher than the first reference-potential generated by the first reference-potential generating unit 106, and the third reference-potential generating unit 112 can generate a third reference-potential lower than the first reference-potential generated by the first reference-potential generating unit 106. Further, the integrating-time timer unit 114b can count an outputting time of the potential integrated by the integrator 111, including the time (discharging time) that reaches a predetermined time from the discharging start time and the time (charging time) that reaches the time when the integrated potential matches the third reference-potential from the charging start time. The charge/discharge control unit 114c can output, to the charge/discharge change-over switch 110, a control signal for switching the connection between the first reference-potential and the second reference-potential and the AC signal of which the phase sensitivity has been detected to discharge the integrator 111 until the time counted by the integrating-time timer unit 114b reaches a predetermined time from the discharging start time. Thereafter, the charge/discharge control unit 114c can further output, to the charge/discharge change-over switch 110, a control signal for switching the connection between the first reference-potential and the second reference-potential and the AC signal of which the phase sensitivity is detected to charge the integrator 111 until the levels of the signals output by the comparator 113 change. The vector-detecting-information calculating unit 114e can calculate a vector detecting information of the AC signal with the known frequency, input by the input amplifier 107, on the basis of the time (the discharging time) that reaches a predetermined time from the discharging start time counted the integrating-time timer unit 114b when the charge/discharge control unit 114c outputs, to the charge/discharge change-over switch 110, the control signal for switching the connection to discharge the integrator 111, the time (the charging time) counted by the integrating-time timer unit 114b when the charge/discharge control unit 114c outputs, to the charge/discharge change-over switch 110, the control signal for switching the connection to charge the integrator 111 until the levels of the signals output by the comparator 113 change, and the two types of phase signals output by the sync-signal control unit 114d.

What is claimed is:

1. A vector detecting device comprising:
a first reference-potential generating unit that generates a first reference-potential;
an input amplifier that receives an AC signal with a known frequency, amplifies or buffers, and outputs the AC signal;
a phase-sensitivity detector that detects a phase sensitivity of the amplified or buffered AC signal using the first reference-potential as a reference;
a second reference-potential generating unit that generates a second reference-potential lower than the first reference-potential;
a charge/discharge change-over switch that switches the connection between the first reference-potential and the second reference-potential and the AC signal of which the phase sensitivity has been detected by the phase-sensitivity detector;
an integrator that integrates the AC signal of which the phase sensitivity has been detected, from the charge/discharge change-over switch, and outputs an integrated potential;
a third reference-potential generating unit that generates a third reference-potential higher than the first reference-potential;
a comparator that outputs signals at levels varying depending on whether the potential output and integrated by the integrator is higher than the third reference-potential or lower than the third reference-potential;
an integrating-time timer unit that counts an outputting time of the potential integrated by the integrator;
a sync-signal control unit that outputs to the phase-sensitivity detector two types of phase signals synchronous with the AC signal with a constant phase thereof;
a charge/discharge control unit that outputs to the charge/discharge change-over switch a control signal for switching the connection between the first reference-potential and the second reference-potential and the AC signal of which the phase sensitivity has been detected to charge the integrator until a time counted by the integrating-time timer unit reaches a predetermined time from a charging start time and, thereafter, a control signal for switching the connection between the first reference-potential and the second reference-potential and the AC signal of which the phase sensitivity has been detected, to discharge the integrator until the levels of the signals output by the comparator change; and
a vector-detecting-information calculating unit that calculates the vector detecting information of the AC signal received by the input amplifier on the basis of a time which reaches the predetermined time from the charging start time counted by the integrating-time timer unit when the charge/discharge control unit outputs to the charge/discharge change-over switch the control signal for switching the connection to charge the integrator, the time counted by the integrating-time timer unit when the charge/discharge control unit outputs to the charge/discharge change-over switch the control signal for switching the connection to discharge the integrator when the levels of the signals output by the comparator change, and the two types of phase signals output by the sync-signal control unit.

2. A vector detecting device comprising:
a first reference-potential generating unit that generates a first reference-potential;
an input amplifier that receives an AC signal with a known frequency, amplifies or buffers, and outputs the AC signal;
a phase-sensitivity detector that detects a phase sensitivity of the amplified or buffered AC signal using the first reference-potential as a reference;
a second reference-potential generating unit that generates a second reference-potential higher than the first reference-potential;
a charge/discharge change-over switch that switches the connection between the first reference-potential and the second reference-potential and the AC signal of which the phase sensitivity has been detected by the phase-sensitivity detector;
an integrator that integrates the AC signal of which the phase sensitivity has been detected, from the charge/discharge change-over switch, and outputs an integrated potential;
a third reference-potential generating unit that generates a third reference-potential lower than the first reference-potential;
a comparator that outputs signals at levels varying depending on whether the potential output and integrated by the integrator is higher than the third reference-potential or lower than the third reference-potential;
an integrating-time timer unit that counts an outputting time of the potential integrated by the integrator;
a sync-signal control unit that outputs to the phase-sensitivity detector two types of phase signals synchronous with the AC signal with a constant phase thereof;
a charge/discharge control unit that outputs to the charge/discharge change-over switch a control signal for switching the connection between the first reference-potential and the second reference-potential and the AC signal of which the phase sensitivity has been detected to discharge the integrator until a time counted by the integrating-time timer unit reaches a predetermined time from a discharging start time and, thereafter, a control signal for switching the connection between the first reference-potential and the second reference-potential and the AC signal of which the phase sensitivity has been detected to charge the integrator until the levels of the signals output by the comparator change; and
a vector-detecting-information calculating unit that outputs vector detecting information of the AC signal received by the input amplifier on the basis of a time which reaches the predetermined time from the discharging start time counted by the integrating-time timer unit when the charge/discharge control unit outputs to the charge/discharge change-over switch the control signal for switching the connection to discharge the integrator, a time counted by the integrating-time timer unit when the charge/discharge control unit outputs to the charge/discharge change-over switch the control signal for switching the connection to charge the integrator when the levels of the signals output by the comparator change, and the two types of phase signals output by the sync-signal control unit.

3. A living-body complex impedance measuring apparatus comprising:
- an AC constant-current signal generating unit that generates a sinusoidal AC constant-current signal with a known frequency;
- a reference impedance connected to the living body serially or in parallel therewith, the sinusoidal AC constant-current signal flows flowing thereto;
- a selector that switches a connection via the living body or the reference impedance;
- a first reference-potential generating unit that generates a first reference-potential;
- an input amplifier that receives the sinusoidal AC constant-current signal via the selector, amplifies or buffers, and outputs the sinusoidal AC constant-current signal;
- a phase-sensitivity detector that detects a phase sensitivity of the amplified or buffered sinusoidal AC constant-current signal by the input amplifier using the first reference-potential, as a reference;
- a second reference-potential generating unit that generates a second reference-potential lower than the first reference-potential;
- a charge/discharge change-over switch that switches the connection between the first reference-potential and the second reference-potential and the sinusoidal AC constant-current signal of which the phase sensitivity has been detected;
- an integrator that integrates the sinusoidal AC constant-current signal of which the phase sensitivity has been detected from the charge/discharge change-over switch, and outputs the integrated potential;
- a third reference-potential generating unit that generates a third reference-potential higher than the first reference-potential;
- a comparator that outputs signals at levels varying depending on whether the potential output and integrated by the integrator is higher than the third reference-potential or lower than the third reference-potential;
- an integrating-time timer unit that counts an outputting time of the potential integrated by the integrator;
- a sync-signal control unit that outputs two types of phase signals synchronous with a sinusoidal AC constant-current signal with a constant phase thereof to the phase-sensitivity detector;
- a charge/discharge control unit that outputs to the charge/discharge change-over switch a control signal for switching the connection between the first reference-potential and the second reference-potential and the sinusoidal AC constant-current signal of which the phase sensitivity has been detected, to charge the integrator until a time counted by the integrating-time timer unit reaches a predetermined time from a charging start time and, thereafter, a control signal for switching the connection between the first reference-potential and the second reference-potential and the sinusoidal AC constant-current signal of which the phase sensitivity has been detected, to discharge the integrator until the levels of the signals output by the comparator change;
- a vector-detecting-information calculating unit that calculates the vector detecting information of the sinusoidal AC constant-current signal received by the input amplifier, on the basis of a time which reaches the predetermined time from the charging start time counted by the integrating-time timer unit when the charge/discharge control unit outputs to the charge/discharge change-over switch the control signal for switching the connection to charge the integrator, a time counted by the integrating-time timer unit when charge/discharge control unit outputs to the charge/discharge change-over switch the control signal for switching the connection to discharge the integrator until the levels of the signals output by the comparator change, and the two types of phase signals output by the sync-signal control unit; and
- a living-body impedance calculating unit that calculates a living-body impedance based on the vector detecting information calculated by the vector-detecting-information calculating unit.

4. A living-body complex impedance measuring apparatus comprising:
- an AC constant-current signal generating unit that generates a sinusoidal AC constant-current signal with a known frequency;
- a reference impedance that is connected to the living body serially or in parallel therewith, the sinusoidal AC constant-current signal flowing thereto;
- a selector that switches the connection via the living body or the reference impedance;
- a first reference-potential generating unit that generates a first reference-potential;
- an input amplifier that receives the sinusoidal AC constant-current signal via the selector, amplifies or buffers, and outputs the sinusoidal AC constant-current signal;
- a phase-sensitivity detector that detects a phase sensitivity of the amplified or buffered sinusoidal AC constant-current signal using the first reference-potential as a reference;
- a second reference-potential generating unit that generates a second reference-potential higher than the first reference-potential;
- a charge/discharge change-over switch that switches the connection between the first reference-potential generated by the first reference-potential and the second reference-potential and the sinusoidal AC constant-current signal of which the phase sensitivity has been detected by the phase-sensitivity detector;
- an integrator that integrates the sinusoidal AC constant-current signal of which the phase sensitivity has been detected from the charge/discharge change-over switch, and outputs an integrated potential;
- a third reference-potential generating unit that generates a third reference-potential lower than the first reference-potential;
- a comparator that outputs signals at levels varying depending on whether the potential integrated and output by the integrator is higher than the third reference-potential or lower than the third reference-potential;
- an integrating-time timer unit that counts an outputting time of the potential integrated by the integrator;
- a sync-signal control unit that outputs two types of phase signals synchronous with the sinusoidal AC constant-current signal with a constant phase thereof to the phase-sensitivity detector;
- a charge/discharge control unit that outputs to the charge/discharge change-over switch a control signal for switching the connection between the first reference-potential and the second reference-potential and the sinusoidal AC constant-current signal of which the phase sensitivity has been detected, to discharge the integrator until a time counted by the integrating-time timer unit reaches a predetermined time from a discharging start time and, thereafter, a control signal for switching the connection between the first reference-potential and the second reference-potential and the sinusoidal AC constant-current signal of which the phase sensitivity has been detected, to charge the integrator until the levels of the signals output by the comparator change;

a vector-detecting-information calculating unit that calculates the vector detecting information of the sinusoidal AC constant-current signal received by the input amplifier on the basis of the time which reaches the predetermined time from the discharging start time counted by the integrating-time timer unit when the charge/discharge control unit outputs to the charge/discharge change-over switch the control signal for switching the connection to discharge the integrator, the time counted by the integrating-time timer unit when the charge/discharge control unit outputs to the charge/discharge change-over switch the control signal for switching the connection to charge the integrator when the levels of the signals output by the comparator change, and the two types of phase signals output by the sync-signal control unit; and a living-body impedance calculating unit that calculates a living-body impedance on the basis of the vector detecting information calculated by the vector-detecting-information calculating unit.

* * * * *